US00PP33317P2

(12) United States Plant Patent
Hansen

(10) Patent No.: US PP33,317 P2
(45) Date of Patent: Aug. 3, 2021

(54) HOSTA PLANT NAMED 'WIND BENEATH MY WINGS'

(50) Latin Name: ***Hosta* hybrid (Tratt.)**
Varietal Denomination: Wind Beneath My Wings

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/974,295

(22) Filed: Dec. 18, 2020

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
See application file for complete search history.

(56) References Cited

PUBLICATIONS http://www.plantsgalore.com/Hostas/cultivars/W/Hosta_Wind_beneath_My_Wings.htm Retrieved from the Internet on Mar. 30, 2021 ,(3 pages total).*

* cited by examiner

*Primary Examiner* — Susan McCormick Ewoldt

(57) ABSTRACT

A new and distinct *Hosta* plant named 'Wind beneath My Wings' with large rounded-mound habit of dense, lanceolate foliage of heavy glaucous bluish-colored above and whitish-blue below, retaining the glaucous covering until the end of summer. Long lanceolate leaves with sharply pointed apices and cordate base have undulate margins and the slightly impressed veins with moderate dimpling between the veins and sinuate margins. The plant has flowers in August with pale lavender outer tepals with the tepals inside distinctly striped in the middle of the tepals with a darker lavender and white on the margins. The new plant is attractive and useful in landscaping as a specimen, in mass, or as a containerized plant by itself or in combination with other plants.

2 Drawing Sheets

Latin name and variety denomination of the plant:
Botanical classification: *Hosta* hybrid (Tratt.).
Variety denomination: 'Wind beneath My Wings'.

STATEMENT REGARDING PRIOR DISCLOSURES UNDER 37 CFR 1.77(B)(6)

*Hosta* 'Wind beneath My Wings' was first introduced by the inventor as a non-enabling description through the International Cultivar Registration Authority registration in early 2020. No plants of *Hosta* 'Wind beneath My Wings' have been sold, in this country or anywhere in the world, nor has any disclosure of the new plant been made, more than one year prior to the filing date of this application.

BACKGROUND AND ORIGIN OF THE PLANT

The present invention relates to a new and distinct *Hosta* plant, *Hosta* 'Wind beneath My Wings' hereinafter also referred to as the new plant or the cultivar name, 'Wind beneath My Wings'. *Hosta* 'Wind beneath My Wings' was hybridized at a wholesale nursery in Zeeland, Mich., USA on Aug. 20, 2011 as a cross between 'Neptune' U.S. Plant Pat. No. 19,670 as the female parent and 'Queen of the Seas' (not patented) as the male parent. The new plant is the selection of as a single seedling among several in that cross identified as 11-55-6 through the trial process. The new plant has been asexually propagated by division at the same nursery in Zeeland, Mich., USA since 2016, and also by careful plant shoot-tip tissue culture, with the resultant asexually propagated plants having retained all the same traits as the original plant.

BRIEF SUMMARY OF THE PLANT

There are over 7,000 registered *Hosta* cultivars with The American *Hosta* Society, which is the International Cultivar Registration Authority for the genus *Hosta* along with a similar number of unregistered cultivars. The nearest comparison cultivars known to the inventor are: 'Blue Angel' (not patented), 'Diamond Lake' U.S. Plant Pat. No. 30,769, 'Joy Ride' (not patented), 'Tears in Heaven' copending U.S. Plant patent application Ser. No. 16/974,298, 'Voices in the Wind' copending U.S. Plant patent application Ser. No. 16/974,296 and 'Waterslide' U.S. Plant Pat. No. 30,303.

'Blue Angel' has more cordate and broader foliage with less glaucous blue, the habit is slightly larger and the scapes are more upright and less arching. 'Diamond Lake' has foliage that is more bullate, cordate with a broader, more rounded leaf with a less pointed apex. 'Joy Ride' is shorter and broader in habit with narrower foliage that is less glaucous and with a coarser undulation. 'Tears in Heaven' has smaller habit and a more folded leaf. 'Neptune' is smaller in habit and leaf size, the leaves are narrower, have a more narrowly acute apex, with less wavy margins. 'Queen of the Seas' is more upright in habit with broader foliage having less glaucous blue foliage and less wavy margins. 'Voices in the Wind' has narrower variegated foliage that is more cupped or folded. 'Waterslide' is smaller in leaf size and habit with more narrow folded foliage.

Other *Hosta* cultivars have glaucous foliage, but 'Wind beneath My Wings' is distinct from the above listed *Hostas* and all other cultivars known to the discoverer by the following combined traits:

1. Large rounded-mound plant with dense foliage;
2. Lanceolate foliage with lateral edges folded upwardly and undulate margins, sharply pointed apices and cordate base;
3. Leaves with heavy glaucous bluish coloring above and glaucous whitish-blue below retained until the end of the summer;
4. Leaves have slightly impressed veins;
5. Tightly-compact pale lavender flowers on arching, glaucous, bluish-colored scapes above foliage.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
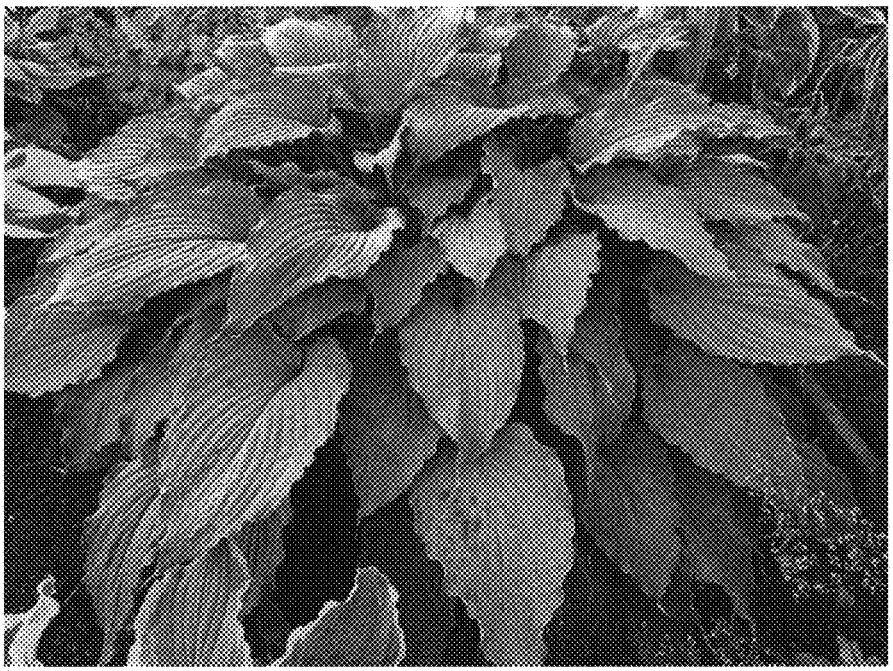
FIG. 1 shows a side view of an eight-year-old plant showing plant habit.
Figure 2:
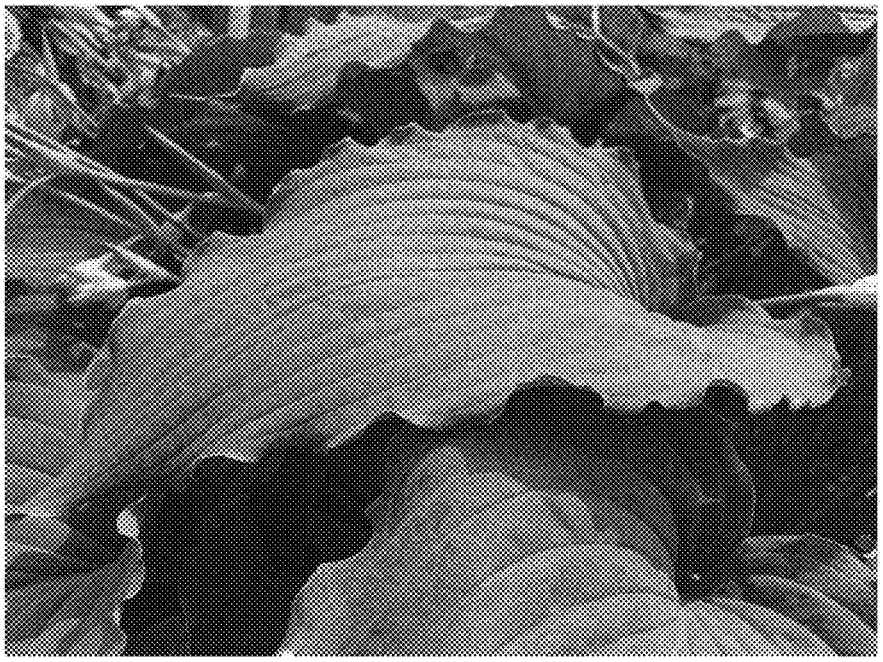
FIG. 2 shows a leaf demonstrating undulate margins, and slightly impressed veins.
Figure 3:
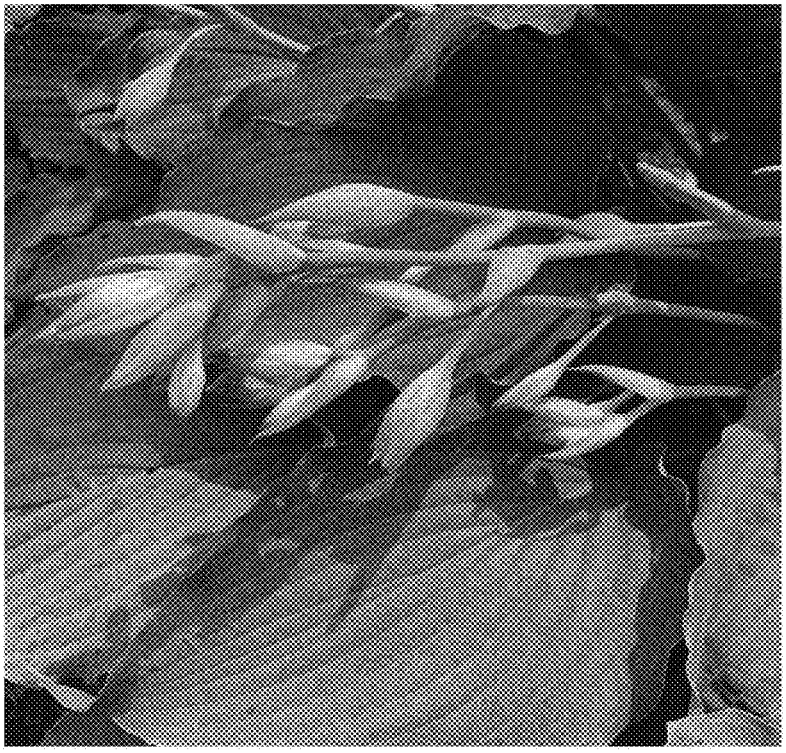
FIG. 3 shows the scapes with opening flower, buds and bracts.
Figure 4:
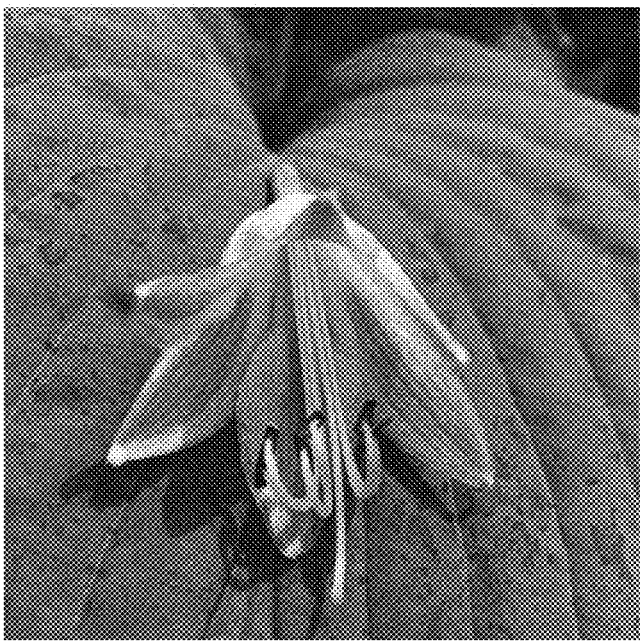
FIG. 4 shows a close-up of the inside of the flower.

The following descriptions and color references are based on the 2015 edition of The Royal Horticultural Society Colour Chart except where common dictionary terms are used. The new plant, *Hosta* 'Wind beneath My Wings', has not been observed under all possible environments. The phenotype may vary slightly with different environmental conditions, such as temperature, light, fertility, moisture and maturity levels, but without any change in the genotype. The following observations and size descriptions are of an eight-year-old plant in a partially shaded trial garden in Zeeland, Mich. with supplemental water and fertilizer.

Botanical classification: *Hosta* x hybrid;

Parentage: 'Neptune' as the female or seed parent, and 'Queen of the Seas' as the male or pollen parent;

Propagation: Garden division and sterile shoot-tip tissue culture;

Time to initiate roots from tissue culture: About two to three weeks;

Growth rate: Rapid;

Crop time: About 10 to 12 weeks to finish during the summer in a one-liter container from rooted tissue culture plantlet;

Rooting habit: Normal, fleshy, lightly branching; color nearest RHS NN155B depending on soil type;

Plant shape and habit: Hardy herbaceous perennial with basal rosette of leaves emerging from rhizomes producing a large, symmetrical, rounded-mound of leaves;

Plant size: Foliage height about 76.2 cm above soil line to the top of the leaves and about 200.7 cm wide at the widest point just above the soil line;

Foliage description: Lanceolate; glabrous, heavily glaucous abaxial and adaxial; with acute to apiculate apex and cordate base; margin entire and undulate; with smooth surfaces, not bullate; mostly flat, without twisting;

Leaf blade size: To about 35.6 cm long, 21.6 cm wide near base; average about 32.5 cm long, 19.5 cm wide;

Leaf blade color: Early season and shortly after emerging adaxial nearest RHS N138B with wax and nearest RHS 137A with wax removed, abaxial blend between RHS 189B and RHS N138C with wax and nearest RHS 137B with wax removed; mid and late season adaxial nearest RHS 137A without wax and between RHS 122B, N138B and RHS 188B with wax, abaxial nearest RHS 137B with wax removed and between RHS N138C, RHS 189B and RHS 122D with wax;

Petiole: Entire, glabrous, glabrous, concavo-convex; mostly outwardly and slightly arching from base of plant to leaf base, strong but flexible; to about 48.0 cm long, 13.0 mm wide at base and 7.0 mm deep at base;

Petiole color: Adaxial center nearest RHS 138C and edges nearest RHS N138C; abaxial center nearest RHS 1385C and edges nearest RHS 138B;

Veins: Parallel; glabrous and glaucous both surfaces; smooth and slightly impressed adaxial, abaxial costate and smooth; typically 10 to 11 pairs and one midrib;

Veins color: Adaxial proximal midrib nearest RHS 138B distal midrib and primary veins between RHS 193A and RHS 122B; abaxial between RHS 188C and RHS 122C with midrib between 138C and RHS 122B;

Flower description:

Buds one day prior to opening: Clavate with acute apex and narrow tubular base; entire bud about 48.0 mm long, with swollen distal portion about 11.0 mm diameter and about 28.0 mm long, base tube about 20.0 mm long and about 3.0 mm diameter; buds slightly smaller distally;

Bud color: Tube basal portion nearest RHS N88D; apical swollen portion nearest RHS N88D with patches of nearest RHS 85C and RHS NN155D, middle portion with bulb and distal corolla tube nearest RHS NN155D;

Flowers: Perfect; single; actinomorphic; funnelform; held slightly drooping to outwardly; about 40.0 mm wide and 67.0 mm long; fused in basal 35.0 mm; corolla to about 57.0 mm long and 40.0 mm wide at apex, tube portion about 22.0 mm long and 3.0 mm diameter (distal flowers smaller); persists for a normal period, usually one day on plant or as cut flower; scapes remain effective with flowers early to late August for about four weeks in Michigan; about 40 flowers per scape;

Floral bracts: Subtending individual flowers; lanceolate; concavo-convex; acute apex; truncate clasping base; glaucous adaxial and abaxial; to about 54.0 mm long and 12.0 mm wide, decreasing distally;

Floral bract color: Adaxial nearest RHS 85A with moderate blushing along edges of nearest RHS 138A; abaxial nearest RHS 86D with moderate blushing nearest RHS 137A;

Flower fragrance: None detected;

Tepal: Six; typically two nearly identical sets of three, glabrous, entire; oblanceolate with acute apex and fused base; to about 58.0 mm long and about 10.0 mm wide above fusion; inner set with transparent distal margin about 1.0 mm wide;

Tepal color: Adaxial edge nearest RHS NN155D and center stripe about 4.0 mm wide nearest RHS 85C and corolla tube nearest RI-IS NN155D in basal 12.0 mm; abaxial edge and corolla tube nearest RHS NN155D including corolla tube and distal center 7 mm wide stripe between RHS 85C and RHS 85D;

Gynoecium: Single; tri-carpelled; 72.0 mm long; exserted;

*Style*.—Single; terete; approximately 66.0 mm long, 0.5 mm diameter, arcuate upward about 90 degrees in distal 6.0 mm; color between RHS 145D and RHS 157D.

*Stigma*.—Globose, micro-puberulent; about 1.0 mm in across and 1.0 mm tall; color nearest RHS 157C.

*Ovary*.—Ellipsoidal; superior; slightly sulcate longitudinally; about 5.5 mm long and 3.0 mm diameter at widest; rounded apex and truncate base; color between RHS 145A and RHS 146D.

Androecium:

*Filaments*.—Typically six; terete; approximately 66.0 mm long and 0.5 mm in diameter; arcuate upward about 120 degrees in the distal 10.0 mm; color between RHS 145D and RHS 157D.

*Anthers*.—Elliptic; dorsifixed, longitudinally dehiscent; about 4.5 mm long and 2.0 mm wide; color nearest RHS 177A unopened and RHS N186B opened.

*Pollen*.—Abundant; elliptic, less than 0.1 mm long; color nearest RHS 21A.

Peduncle: Terete; usually one per mature division and twelve per plant; glaucous, glabrous; slightly outwardly arching; to about 78.0 cm long, and about 7.0 mm in diameter at base; average about 72.0 cm and 6.5 mm diameter, flowering portion about 30.0 cm long;

Peduncle color: When flowering between RHS 145A and RHS 146D;

Pedicel: Glabrous; glaucous; terete; secund, slightly curved downwardly; variable, from 15.0 mm to 27.0 mm long and 1.5 mm to 2.0 mm diameter, decreasing in size distally;

Pedicel color: Between RHS 155D and RHS 145D;

Fruit: Oblong ellipsoid, with acute apex; truncate base; tri-valved dehiscent capsule; about 24.0 cm long and 5.0 mm diameter; color when young nearest RHS 146B blushed moderately with nearest RHS N186B, mature nearest RHS 161C;

Seed: Typically about 36 seeds per capsule; endospermic; flattened-elliptic wing surrounding embryo situated toward one end of ellipse; about 10.0 mm long and 3.0 mm wide and 1.5 thick; color nearest RHS 202A;

Disease tolerance and resistance: The new plant has not shown any resistance to pests and diseases common to *Hostas*.

Growth conditions: The new plant grows best and shows best coloration with plenty of moisture, adequate drainage and light shade, but is able to tolerate some drought when mature, and tolerates direct sun without leaf bum, especially during the cooler parts of the day and when provided sufficient water. Hardiness at least from USDA zone 3 through 9, and other disease resistance is typical of that of other *Hostas*.

It is claimed:

1. A new and distinct ornamental plant cultivar named *Hosta* 'Wind beneath My Wings' as herein described and illustrated.

* * * * *